United States Patent
Saeki et al.

(10) Patent No.: US 8,823,408 B2
(45) Date of Patent: Sep. 2, 2014

(54) SYSTEM AND METHOD FOR EVALUATING ORGANIC MATERIAL FOR ORGANIC SOLAR CELL

(75) Inventors: Akinori Saeki, Suita (JP); Shuhei Seki, Suita (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 14/238,529

(22) PCT Filed: Mar. 8, 2012

(86) PCT No.: PCT/JP2012/055993
§ 371 (c)(1),
(2), (4) Date: Feb. 12, 2014

(87) PCT Pub. No.: WO2013/024602
PCT Pub. Date: Feb. 21, 2013

(65) Prior Publication Data
US 2014/0210452 A1  Jul. 31, 2014

(30) Foreign Application Priority Data
Aug. 15, 2011 (JP) .................. 2011-177637

(51) Int. Cl.
| | |
|---|---|
| *G01R 31/26* | (2014.01) |
| *H01L 31/00* | (2006.01) |
| *G01N 27/00* | (2006.01) |
| *H01L 51/00* | (2006.01) |
| *H01L 31/0256* | (2006.01) |

(52) U.S. Cl.
CPC ............ *G01N 27/00* (2013.01); *H01L 51/0092* (2013.01); *H01L 51/0064* (2013.01); *G01R 31/26* (2013.01); *G01R 31/2605* (2013.01); *H01L 31/0256* (2013.01)
USPC .................. 324/761.01; 324/750.14; 136/252; 136/256; 136/263

(58) Field of Classification Search
CPC .. G01R 31/26; G01R 31/405; G01R 31/2605; H01L 31/0256; H01L 51/0064; H01L 51/0092
See application file for complete search history.

(56) References Cited

U.S. PATENT DOCUMENTS

| | | | | |
|---|---|---|---|---|
| 8,642,720 B2 * | 2/2014 | Onaka et al. | ................ | 528/380 |
| 8,647,708 B2 * | 2/2014 | Kobayashi et al. | ........... | 136/263 |

FOREIGN PATENT DOCUMENTS

| | | | |
|---|---|---|---|
| JP | 06-097248 A | 4/1994 | |
| JP | 11-312718 A | 11/1999 | |

(Continued)

OTHER PUBLICATIONS

Green, Martin, A., et al, "Solar cell efficiency tables (version 35)", Progress in Photovoltaics: Research and Applications, John Wiley & Sons, Ltd., Apr. 2010, pp. 144-150.

(Continued)

*Primary Examiner* — Jermele M Hollington
(74) *Attorney, Agent, or Firm* — Westerman, Hattori, Daniels & Adrian, LLP

(57) ABSTRACT

An evaluation system 1 according to the present invention includes: a light source 2 for exposing a pulsed white light or a pulsed laser light onto a sample; a microwave exposing and detecting unit 8 for exposing a microwave onto an organic material 12 and for detecting the intensity of the microwave which has passed through the organic material 12; a microwave passing unit 7 for making the microwave pass through the organic material 12 a plurality of times; and an evaluating unit 10 for evaluating the photoelectric conversion characteristics of the sample based on the intensity of the microwave which has passed through the organic material 12 when the pulsed white light or the pulsed laser light is exposed and the intensity of the microwave which has passed through the organic material 12 when the pulsed white light or the pulsed laser light is not exposed.

6 Claims, 5 Drawing Sheets

(56) References Cited

FOREIGN PATENT DOCUMENTS

| JP | 2010-272674 A | 12/2010 |
|---|---|---|
| JP | 2010-287849 A | 12/2010 |
| WO | 2010/118004 A1 | 10/2010 |

OTHER PUBLICATIONS

Sariciftci, N., S., et al., "Photoinduced Electron Transfer from a Conducting Polymer to Buckminsterfullerene", Science, Nov. 27, 1992, vol. 258, pp. 1474-1476.

Saeki, Akinori, et al., "Direct Evaluation of Optoelectronic Property of BHJ Layer by Microwave Conductivity", Extended Abstract of the 58th Spring Meeting, The Japan Society of Applied Physics and the Related Societies, Japan, Mar. 9, 2011, P. Rombunno, 24p-BD-16.

Saeki, Akinori, et al., "Direct Evalution of Organic Photovoltaic Cell by Time-Resolved Microwave Conductivity", Polymer Preprints, Japan, 2011, vol. 60, No. 1, P. Rombuno, 3L08, Japanese Office Action dated Sep. 25, 2012 and Japanese Office Action dated Apr. 2, 2013.

Saeki, Akinori, et al., "Charge Transport Property in Self-Organized Materials Studied by Microwave Technique", Kagaku Kogyosha, Inc, Japan, Jul. 1, 2011, vol. 62, No. 7, pp. 494-502, Japanese Office Action dated Sep. 25, 2012.

Japanese Office Action, dated Sep. 25, 2012, issued in corresponding application No. JP2012-531930, w/English translation.

Japanese Office Action, dated Apr. 2, 2013, issued in corresponding application No. JP2012-531930, w/English translation.

Saeki, Akinori, et al., "Electrodeless Meaurement of Charge Carrier Mobility Probed by Microwave", Radiation Chemistry, Japan, 2006, No. 81, pp. 29-39, cited in Japanese Office Action dated Apr. 2, 2013.

International Search Report, dated May 29, 2012, issued in corresponding application No. PCT/JP2012/055993.

Extended European Search Report dated Apr. 4, 2014, issued in corresponding European Patent Application No. 12823455.6 (8 pages).

Akinori S. et al., "Electrodeless measurement of charge carrier mobility in pentacene by microwave and optical spectroscopy techniques", Journal of Applied Physics, vol. 100, No. 2, 023703, (2006), pp. 1-6, Extended European Search Report dated Apr. 4, 2014.

Savenije T. J. et al., "A time-resolved microwave conductivity study of the optoelectronic processes in TiO2|In2S3| CuInS2 heterojunctions", Journal of Applied Physics, vol. 101, No. 11, 113718, (2007), pp. 1-7, Extended European Search Report dated Apr. 4, 2014.

Gutmann R. J. et al., "Microwave-detected photoconductivity-transient spectroscopy for non-destructive evaluation of GaAs wafers", Proceedings of SPIE, vol. 0794, (1987), pp. 128-135, Extended European Search Report dated Apr. 4, 2014.

Akinori S. et al., "Direct Evaluation of Intrinsic Optoelectronic Performance of Organic Photovoltaic Cells with Minimizing Impurity and Degradation Effects", Advanced Energy Meterials, vol. 1, No. 4, (2011), pp. 661-669, Extended European Search Report dated Apr. 4, 2014.

* cited by examiner

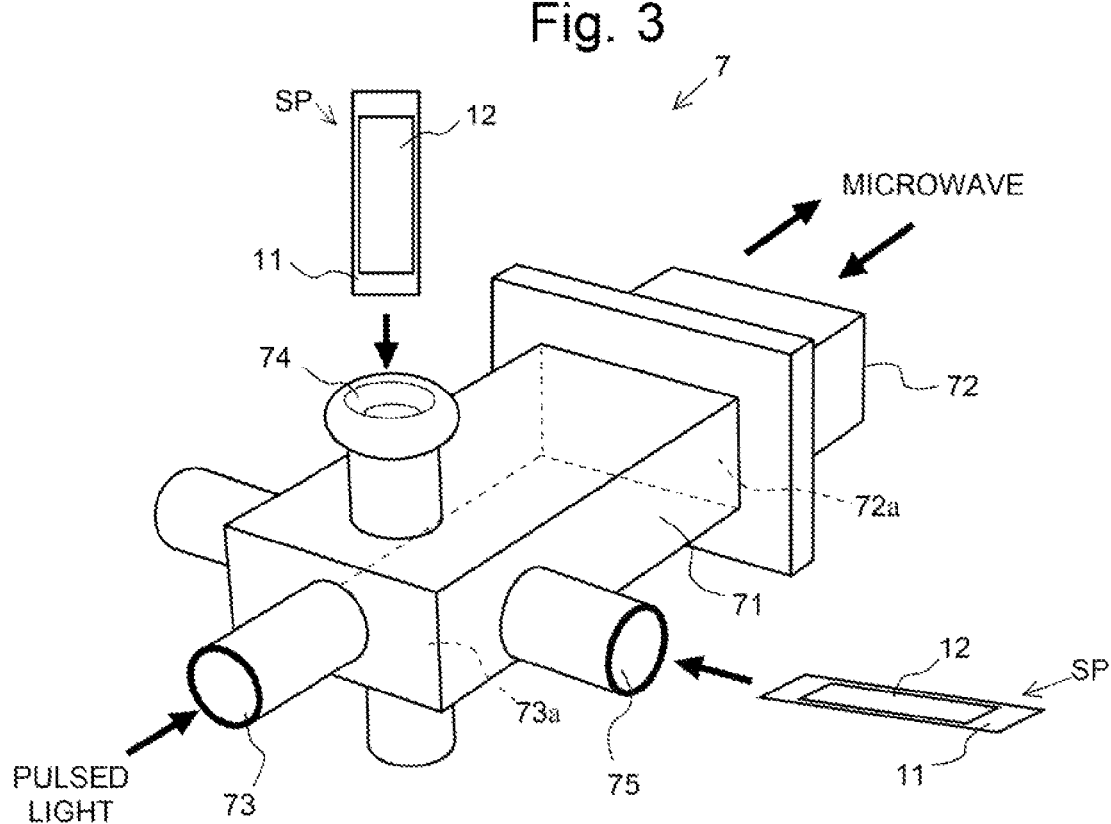

SYSTEM AND METHOD FOR EVALUATING ORGANIC MATERIAL FOR ORGANIC SOLAR CELL

TECHNICAL FIELD

The present invention relates to a system and method for evaluating photoelectric conversion characteristics of organic materials used in organic solar cells, such as organic thin-film solar cells or dye-sensitized solar cells.

BACKGROUND ART

All of the solar cells currently used in households and large-scale power generation facilities are inorganic solar cells using silicon, CuInSe or other kinds of inorganic compound semiconductors. The efficiency of photoelectric conversion from sunlight energy into electric energy by such solar cells is within a range from 10 to 20% (for example, see Non-Patent Document 1). However, inorganic solar cells are expensive due to the costly process of silicon crystallization and film formation. To recover initial investments, it is necessary to further improve their photoelectric conversion efficiency and lower their production cost.

Meanwhile, organic solar cells, such as organic thin-film solar cells or dye-sensitized solar cells, which use organic substances as active layers or charge transport materials, are expected to be the next generation of solar cells since they are inexpensive and they can be used for realizing lightweight, flexible power generation devices. Accordingly, a number of worldwide industrial organizations, research institutes and universities have been conducting research on organic solar cells from various perspectives, such as the development of new materials for organic solar cells, the improvement of the production process, the optimization of the device structure, the enlargement of the device area, and the application of a high-productivity process using the Roll-to-Roll system.

In particular, an organic thin-film solar cell called the Bulk Heterojunction (BHJ) type is ranked as one of the most promising next-generation solar cells since it has the potential of being produced at even lower costs due to the simple production process and the availability of various organic materials (for example, see Non-Patent Document 2). The BHJ type organic thin-film solar cell has a power generation layer composed of a mixture of a high-molecular donor material and an acceptor material, where the high-molecular donor material and the acceptor material are phase-separated from each other on a nanoscale, allowing electric charges to be easily separated. Well-known examples of the acceptor material are fullerene derivatives (typically, [6,6]-Phenyl-$C_{61}$-Butyric Acid Methyl Ester, or PCBM).

FIG. 7 is a schematic diagram for explaining the principle of photoelectric conversion by a BHJ type organic thin-film solar cell 100. The BHJ type organic thin-film solar cell 100 is formed by mixing a high-molecular donor 101 with an acceptor 102 made of a fullerene derivative (typically, PCBM). When a ray of light impinges on the donor 101, an exciton consisting of a positive hole and an electron combined as one pair is generated. The exciton diffuses to the junction plane, where the pair is dissociated into free carriers. The generated electron moves into the acceptor 102, to be extracted through an electrode 104, while the positive hole is extracted through an electrode 103 of the donor 101.

BACKGROUND ART DOCUMENT

Non-Patent Document

Non-Patent Document 1: Martin A. Green et. al., *Progress Photovoltaics Res. Appl.* 2010, p. 144-150, 2010

Non-Patent Document 2: N. S. Sariciftci et. al., SCIENCE VOL. 258, p. 1474-1476, 1992

SUMMARY OF THE INVENTION

Problem to be Solved by the Invention

However, as compared to inorganic solar cells, organic solar cells have lower photoelectric conversion efficiencies (approximately 3-9%), and furthermore, they are less durable. To improve their photoelectric conversion efficiency and durability, it is essential to develop a new organic material available for organic solar cells.

Evaluation of a new organic material is performed by evaluating the performance of an organic thin-film solar cell produced by using that organic material. However, there are problems resulting from the very use of the organic material.

One problem is that, since metallic catalysts and impurities remain in the cross-coupling reaction, substituent addition reaction or other reactions, the charge carriers generated by irradiation with the sunlight become trapped at the impurities as well as at intramolecular and intermolecular structural defects or grain boundaries, with the result that the value of the electric current produced by charge carriers upon reaching the electrodes decreases. Another problem is that, as compared to the case of the inorganic solar cells, an overwhelmingly large number of parameters must be optimized to determine the true performance, since organic materials significantly vary in chemical and physical structures. Particularly serious problems are the presence of the trapping sites at the interface between the organic material and the electrode as well as the segregation of the donor and acceptor materials in the process of forming the BHJ layer.

Normally, a direct-current (DC) method (such as a time-of-flight (TOF) method or field-effect transistor (FET) method) is used for the measurement of the mobility of charge carriers in an organic semiconductor where the photoelectric conversion takes place. In the case of the TOF and FET methods, since the charge carriers are made to move a long distance (a few μm to several hundred μm) between the electrodes under a high electric field ($10^5$ to $10^6$ V/cm), their motion is strongly affected by various factors, such as the barrier at the interface between the electrode and the organic semiconductor or a number of trapping sites (impurities, structural defects and grain boundaries) in the system. Therefore, even if the material itself has a high degree of carrier mobility, the average mobility over the entire sample as measured by the TOF or FET method will be low since the aforementioned factors make the mobility lower.

This means that the mobility of charge carriers to be measured fluctuates by many orders of magnitudes depending on the conditions under which a sample for the performance evaluation is produced, i.e. the presence or absence of the mixture of oxygen, the film morphology (in the case of a wet process, the grain size, the molecular orientation and the crystallinity significantly change depending on various conditions, such as the kind of solvent, the concentration of solution, the method of the substrate temperature, the exposing method and the substrate treatment), the distance between the electrodes, the device structure, and the volume of the residual solvent.

Therefore, in the process of sample preparation, after an organic material is applied, the organic material must be carefully prepared in a finely controlled glove box so as to prevent dust or scratches which may possibly cause short-circuiting or lower the output level as well as to prevent voids (pin-holes) from being formed in the solvent-removing process, after which an electrode must be deposited on the organic material (photoelectric conversion layer), which takes a long period of time (1-4 hours).

Thus, the conventional performance evaluation of an organic solar cell is easily affected by impurities and other external factors, so that it is extremely difficult to directly evaluate the performance of the organic material. Furthermore, a considerable amount of time and labor is required for the performance evaluation.

The present invention has been developed to solve the previously described problems, and its objective is to realize a system and method for evaluating an organic material for an organic solar cell by which the photoelectric conversion characteristics of an organic material for an organic solar cell can be quickly and easily evaluated.

Means for Solving the Problem

An evaluation system for evaluating an organic material for an organic solar cell according to the present invention aimed at solving the previously described problems is an evaluation system for evaluating photoelectric conversion characteristics of an organic material used in an organic solar cell, including:

a microwave exposing section for exposing a microwave onto the organic material;

a microwave passing section for making the microwave exposure from the microwave exposing section pass through the organic material a plurality of times;

a light source section for exposing a pulsed white light onto the organic material;

a microwave detecting section for detecting the intensity of the microwave which has passed through the organic material; and an evaluating section for evaluating the photoelectric conversion characteristics of the organic material based on the intensity of the microwave which has passed through the organic material when the pulsed white light is exposed and the intensity of the microwave which has passed through the organic material when the pulsed white light is not exposed.

Another evaluation system for evaluating an organic material for an organic solar cell according to the present invention aimed at solving the previously described problems is an evaluation system for evaluating photoelectric conversion characteristics of an organic material used in an organic solar cell, including:

a microwave exposing section for exposing a microwave onto the organic material;

a microwave passing section for making the microwave exposure from the microwave exposing section pass through the organic material a plurality of times;

a light source section for exposing, onto the organic material, a pulsed laser light having a wavelength within a range of wavelengths of sunlight;

a microwave detecting section for detecting the intensity of the microwave which has passed through the organic material; and an evaluating section for evaluating the photoelectric conversion characteristics of the organic material based on the intensity of the microwave which has passed through the organic material when the pulsed laser light is exposed and the intensity of the microwave which has passed through the organic material when the pulsed laser light is not exposed.

An evaluation method for evaluating an organic material for an organic solar cell according to the present invention aimed at solving the previously described problems is an evaluation method for evaluating photoelectric conversion characteristics of an organic material used in an organic solar cell, including:

a microwave exposing step, in which a microwave is exposed onto the organic material;

a microwave passing step, in which the microwave exposure in the microwave exposing step is made to pass through the organic material a plurality of times;

a light exposing step, in which a pulsed white light is exposed onto the organic material;

a microwave detecting step, in which the intensity of the microwave which has passed through the organic material is detected; and an evaluating step, in which the photoelectric conversion characteristics of the organic material are evaluated based on the intensity of the microwave which has passed through the organic material when the pulsed white light is exposed and the intensity of the microwave which has passed through the organic material when the pulsed white light is not exposed.

Another evaluation method for evaluating an organic material for an organic solar cell according to the present invention aimed at solving the previously described problems is an evaluation method for evaluating photoelectric conversion characteristics of an organic material used in an organic solar cell, including:

a microwave exposing step, in which a microwave is exposed onto the organic material;

a microwave passing step, in which the microwave exposure in the microwave exposing step is made to pass through the organic material a plurality of times;

a light exposing step, in which a pulsed laser light having a wavelength within a range of wavelengths of sunlight is exposed onto the organic material;

a microwave detecting step, in which the intensity of the microwave which has passed through the organic material is detected; and an evaluating step, in which the photoelectric conversion characteristics of the organic material is evaluated based on the intensity of the microwave which has passed through the organic material when the pulsed laser light is exposed and the intensity of the microwave which has passed through the organic material when the pulsed laser light is not exposed.

In the previously described configuration, a pulsed white light or a pulsed laser light having a wavelength within a range of wavelengths of sunlight (the pulsed white light and the pulsed laser light are hereinafter collectively called in this paragraph the "pulsed light") is exposed onto an organic material under the condition that a microwave is being exposed onto the organic material. If this material has photoresponse to the light within a wavelength range of sunlight, charge carriers are generated in the organic material. These charge carriers absorb the microwave. Therefore, every time the microwave passes through the organic material, the intensity of the microwave is attenuated as compared to the intensity detected when the pulsed light is not exposed. The amount of attenuation of the microwave by one passage of the microwave through the organic material is small. However, as the microwave is made to pass through the organic material in a cavity a plurality of times, the microwave will be eventually attenuated by a large amount by the charge carriers. Therefore, it is possible to accurately detect the amount of attenuation of the microwave due to the charge carriers by comparing the intensity of the microwave detected when the pulsed light is exposed and the intensity of the microwave detected when the pulsed light is not exposed. In this case, the evaluation can be made such that the larger the amount of attenuation is, the better the photoelectric conversion characteristics of the organic material are.

Information about the period of time required for the charge carriers to recombine can be obtained by detecting the intensities of the microwave immediately after the exposure to the pulsed light and after nanoseconds to microseconds. In this case, the evaluation can be made such that the longer the period of time required for the charge carriers to recombine is (i.e. the slower the temporal change in the intensity of the microwave immediately after the exposure to the pulsed light), the better the photoelectric conversion characteristics of the organic material are.

Thus, with the present invention, it is possible to accurately evaluate the photoelectric conversion characteristics of an organic material based on the amount of attenuation of the microwave due to the charge carriers as well as the information on the period of time required for the charge carriers to recombine.

The photoelectric conversion characteristics of the organic material can be evaluated based on the amount of attenuation of the microwave. Therefore, unlike the conventional system, it is unnecessary to form an electrode on the organic material in order to evaluate the performance of the material. Furthermore, there is no need to purify the material since the influence of impurities is limited; for example, even an organic material simply applied on a substrate by a spin-coating process in the air can be evaluated. Consequently, the time and labor for the evaluation will be dramatically reduced.

Thus, according to the present invention, an evaluation system and method capable of quickly and easily evaluating photoelectric conversion characteristics of an organic material for an organic solar cell can be realized.

In particular, the system using a pulsed white light can provide information which directly reflects the actual photoelectric conversion characteristics since the light has a spectrum close to sunlight.

Effect of the Invention

As described thus far, the evaluation system for evaluating an organic material for an organic solar cell according to the present invention is an evaluation system for evaluating photoelectric conversion characteristics of an organic material used in an organic solar cell, including: a microwave exposing section for exposing a microwave onto the organic material; a microwave passing section for making the microwave exposure from the microwave exposing section pass through the organic material a plurality of times; a light source section for exposing, onto the organic material, a pulsed white light or a pulsed laser light having a wavelength within a range of wavelengths of sunlight; a microwave detecting section for detecting the intensity of the microwave which has passed through the organic material; and an evaluating section for evaluating the photoelectric conversion characteristics of the organic material based on the intensity of the microwave which has passed through the organic material when the pulsed white light or pulsed laser light is exposed and the intensity of the microwave which has passed through the organic material when the pulsed white light or pulsed laser light is not exposed.

The evaluation method for evaluating an organic material for an organic solar cell according to the present invention is an evaluation method for evaluating photoelectric conversion characteristics of an organic material used in an organic solar cell, including: a microwave exposing step, in which a microwave is exposed onto the organic material; a microwave passing step, in which the microwave exposed in the microwave exposing step is made to pass through the organic material a plurality of times; a light exposing step, in which a pulsed white light or a pulsed laser light having a wavelength within a range of wavelengths of sunlight is exposed onto the organic material: a microwave detecting step, in which the intensity of the microwave which has passed through the organic material is detected; and an evaluating step, in which the photoelectric conversion characteristics of the organic material are evaluated based on the intensity of the microwave which has passed through the organic material when the pulsed white light or the pulsed laser light is exposed and the intensity of the microwave which has passed through the organic material when the pulsed white light or the pulsed laser light is not exposed. Accordingly, it is possible to realize an evaluation system and method capable of quickly and easily evaluating the photoelectric conversion characteristics of an organic material for an organic solar cell.

BRIEF DESCRIPTION OF THE DRAWINGS

FIG. 3 shows the construction of a microwave passing unit.

MODE FOR CARRYING OUT THE INVENTION

Embodiment 1

The first embodiment of the present invention is hereinafter described on the basis of FIGS. 1-4C.

(System Configuration)

Figure 1:
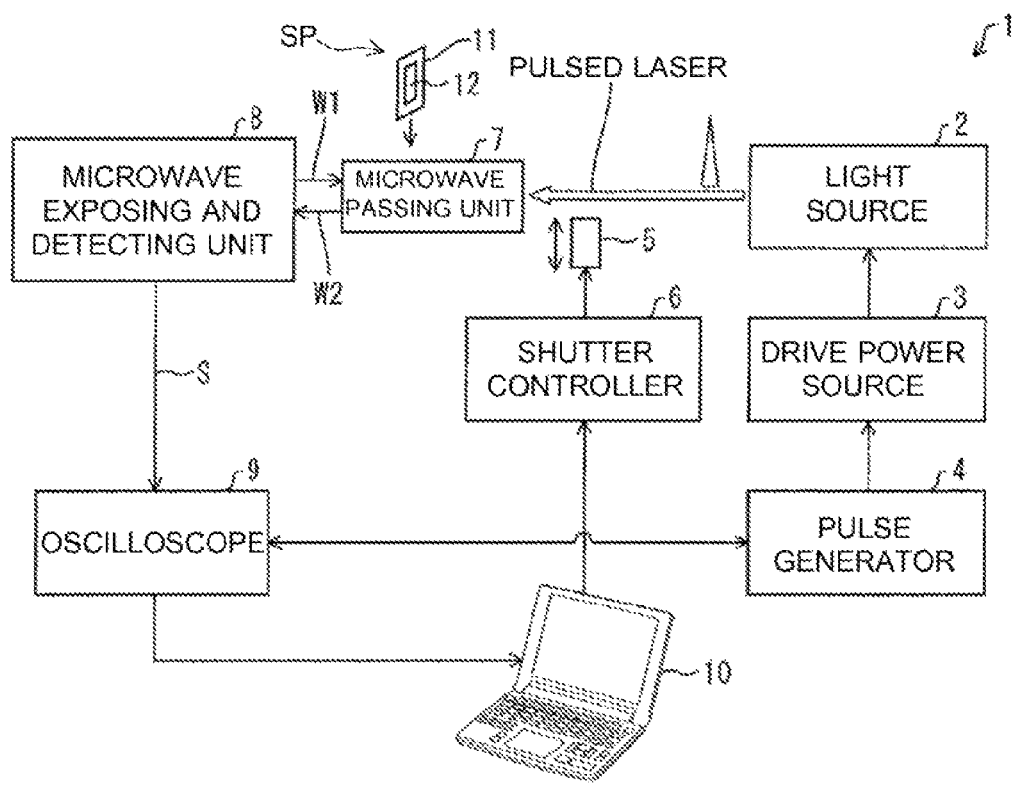
FIG. 1 is a diagram showing the configuration of an evaluation system according to the first embodiment of the present invention.

FIG. 1 is a diagram showing the configuration of an evaluation system 1 according to the present embodiment. The evaluation system 1 includes a light source 2, a drive power source 3, a pulse generator 4, a shutter 5, a shutter controller 6, a microwave passing unit 7, a microwave irradiating and detecting unit 8, an oscilloscope 9 and an evaluating unit 10.

In the present embodiment, the light source 2 includes a laser light source. The microwave passing unit 7 includes a cavity resonator. The microwave irradiating and detecting unit 8 includes a microwave circuit. The evaluating unit 10 includes a controlling and analyzing computer. The microwave circuit has the functions of generating a microwave, guiding the microwave to the cavity resonator and detecting the intensity of the microwave reflected by the cavity resonator. For example, the microwave circuit consists of a Gunn oscillator, an attenuator, a phase shifter, a waveguide, a frequency counter, a microwave detector, an amplifier, a directional coupler, a circulator, a coaxial cable and other components.

Figure 2:
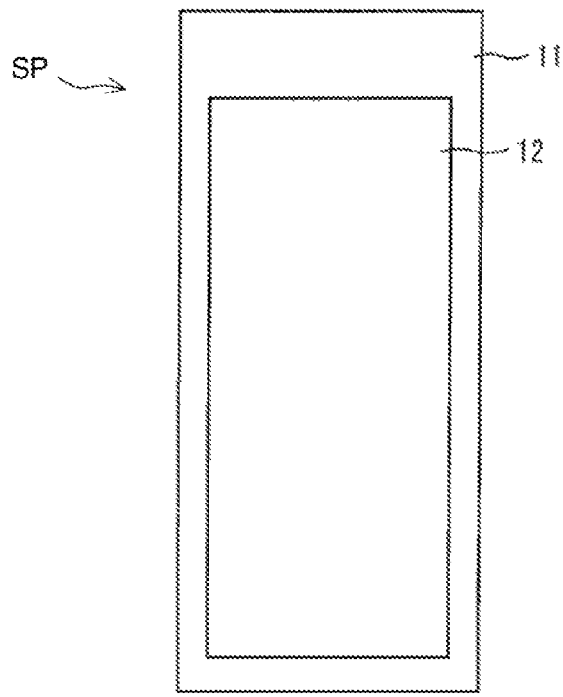
FIG. 2 shows one example of a sample to be evaluated.

FIG. 2 is a diagram showing one example of the sample SP to be set in the microwave passing unit 7. The sample SP is a quartz substrate 11 on which an organic material 12 is applied by spin-coating. Unlike a sample used in a conventional evaluation system, no electrode is formed on it.

FIG. 3 shows the cavity resonator in the microwave passing unit 7. This cavity resonator includes a resonation unit 71 shaped like a rectangular tube having a microwave introduction port 72 at one end and a pulsed-light inlet 73 at the other end, with two sample insertion openings 74 and 75 through which a sample SP is to be inserted into the resonation unit 71. The sample insertion opening 74 vertically penetrates the resonation unit 71, while the sample insertion opening 75 horizontally penetrates the resonation unit 71. The two sample insertion openings 74 and 75 allow the sample SP to be inserted vertically and horizontally into the resonation unit 71, respectively. Accordingly, when a microwave is supplied into the resonation unit 71, an organic material 12 put on the quartz substrate 11 can be evaluated in terms of the photoelectric conversion characteristics in different directions.

After the sample SP is set in the microwave passing unit 7 of the evaluation system 1, a microwave W1 is exposed from the microwave exposing and detecting unit 8 into the microwave passing unit 7 (microwave exposing step). This microwave is introduced through the microwave introduction port 72 of the microwave passing unit 7 into the resonation unit 71, where only a component of the microwave whose wavelength satisfies resonance conditions reaches the organic material 12 and passes through the same material 12 (microwave passing step). After passing through the organic material 12, the microwave W1 is reflected by an inner end face 73a opposite from the microwave introduction port 72 of the resonation unit 71 (i.e. by the end face on the side where the pulsed-light inlet 73 is located). The reflected microwave W1 once more passes through the organic material 12, after which it is reflected by the inner end face 72a on the side where the microwave introduction port 72 of the resonation unit 71 is located. Thus, the microwave W1 is reflected by the inner end faces 72a and 73a at both ends of the resonation unit 71, traveling back and forth a plurality of times within the resonation unit 71. After passing through the organic material 12 a certain number of times (e.g. 2000 to 3000 times), the microwave is made to exit through the microwave introduction port 72 toward the microwave exposing and detecting unit 8. (The microwave exiting from the resonation unit 71 after passing through the organic material 12 is hereinafter called the "microwave W2.") It should be noted that the wavelength of the microwave component which resonates with the resonation unit 71 of the microwave passing unit 7 is determined by the shape and size of the resonation unit 71 and can be appropriately changed by measurers.

While the microwave W1 is traveling back and forth within the resonation unit 71, the light source 2 is driven by the drive power source 3. Subsequently, the shutter 5, which is initially positioned between the light source 2 and the microwave passing unit 7, is moved under the control of the shutter controller 6 so as to let a pulsed laser light from the light source 2 be exposed onto the sample SP inside the resonation unit 71 (light exposing step). The timing and repetition frequency of the exposure of the pulsed laser light are controlled by the pulse generator 4. The wavelength of the pulsed laser light can also be set stepwise within a range from 355 to 700 nm. There is no specific limitation on the wavelength of the pulsed laser light as long as it is within the range of wavelengths of sunlight.

When the pulsed laser light is exposed onto the sample SP, charge carriers are generated in the organic material 12 of the sample SP. Since those charge carriers absorb the microwave, the intensity of the microwave W2 exiting from the resonation unit 71 after passing through the organic material 12 becomes lower than in the case where the pulsed laser light is not exposed. That is to say, the amount of attenuation (power loss) of the microwave as compared to the level measured with no laser exposure changes depending on the amount of charge carriers.

The intensity of the microwave W2 exiting from the microwave passing unit 7 (resonation unit 71) is detected by the microwave exposing and detecting unit 8 (microwave detecting step). A signal S which indicates the intensity of the detected microwave is sent through the oscilloscope 9 to the evaluating unit 10. In the evaluating unit 10, the intensity of the microwave W2 detected when the pulsed laser light was exposed and that of the microwave W2 detected when the pulsed laser light was not exposed are compared to calculate the amount of attenuation of the microwave due to the charge carriers and to evaluate the photoelectric conversion characteristics of the sample based on the amount of attenuation (evaluating step). Specifically, the evaluation is made such that the larger the amount of attenuation (power loss) of the microwave is, and the slower the attenuation is (i.e. the larger the area under the attenuation curve in FIG. 4C is), the better photoelectric conversion characteristics of the sample are.

Although the amount of attenuation of the microwave caused by one passage of the microwave through the organic material 12 is small, the microwave passing unit 7 can increase the amount of attenuation of the microwave due to the charge carriers by making the microwave pass through the organic material 12 a plurality of times (which is practically within a range from 2000 to 3000). Therefore, the microwave exposing and detecting unit 8 can accurately detect the amount of attenuation of the microwave due to the charge carriers. Based on this amount of attenuation, the evaluating unit 10 evaluates the photoelectric conversion characteristics of the organic material 12.

(Principle of Evaluation)

As described thus far, in the evaluation system 1 according to the present embodiment, the time-resolved microwave conductivity (TRMC) measurement method is applied to the performance evaluation of an organic thin-film solar cell. Experimentally, it is the power loss that is detected in the present measurement method. The detected power loss corresponds to a dielectric loss when induced dipoles are involved in the process or to an electric conductivity when charge carriers are involved. The contribution of the power loss significantly varies depending on the phase of the system (gas, liquid or solid), the experimental conditions (gas pressure, gas species and microwave power) and the kind of material. Accordingly, it is possible to select the experimental conditions, the microwave circuit, and other factors so that the power loss can be correctly measured.

Electric conductivity and charge carrier mobility are known as two of the physical quantities which show device performances (photoelectric conversion characteristics). The electric conductivity $\sigma$ (S/cm) is expressed as the product of the charge carrier mobility $\mu$ ($cm^2$/Vs) and the charge carrier density n (/$cm^3$), $\sigma = e\Sigma n\mu$ (where e is the elementary electric charge). The reason why the product of n and µ is expressed as the sum using Σ is because there are positive and negative charge carriers and the two types of carriers have different densities and mobilities inside the device. The higher the charge-carrier mobility is, the quicker the device responds. If the electric-field strength is the same, a higher charge-carrier mobility leads to a larger amount of electric current.

Unlike the DC methods (e.g. the TOF or FET method) conventionally used for the evaluation, the evaluation method according to the present embodiment is an alternating-current (AC) method using a microwave as a probe and can measure photoelectric conversion characteristics without requiring an electrode to be formed on a sample. Since the present method is free from the problems associated with the contact at the electrode interface, it is possible to easily obtain pure photoelectric conversion characteristics which strongly reflect nanoscale properties of the organic material itself, such as the interface, form (morphology and intermolecular interaction) and structure (supermolecular structure and main-chain structure of high polymer). Furthermore, by dissolving the organic material in a non-polar solvent, the intermolecular interactions can be eliminated to measure only the intramolecular electric conductivity.

In the present embodiment, since a high-frequency wave on the order of a few GHz to several tens of GHz and a nanosecond pulsed laser light are used, the TRMC signal at the end of the pulse (with a time resolution of one through several tens of nanoseconds) reflects the mobility within micro-size regions where a large amount of charge carriers still remain without being captured in the trapping sites. Accordingly, the influence of the impurities or other factors is limited to a minimum.

Furthermore, since the electric-field strength is extremely low ($10^{-1}$ to $10^1$ V/cm), it is possible to build a model without including complex factors, such as the influence of a local potential acting on the charge carriers in the material and a thermal activation process, as represented by the Poole-Frenkel model. If the sample is a polar solvent or similar material having a large dipole moment (a high dielectric constant), or a metal or similar material having a large amount of free electrons, the sample is not suitable for the measurement since the material itself absorbs microwaves. If this situation does not exist, the sample can directly be used in the measurement in various forms, such as a solution, film or powder.

In the conventional evaluation method, the sample preparation process includes purifying the material by performing column purification, soxhlet extraction, metallic catalyst removal and other processes, which takes approximately one week. After an organic material is applied, the preparing task must be carefully performed in a finely controlled glove box so as to prevent dust or scratches which may possibly cause short-circuiting or lower the output level, after which an electrode must be deposited, which takes 1-4 hours. By contrast, in the evaluation method according to the present embodiment, there is no need to purify the material since the influence of impurities is limited; what is necessary is to simply apply an organic material on a quartz substrate by a spin-coating process in the air. Furthermore, the sample can be prepared in a shorter period of time since there is no need to form an electrode. Therefore, the sample preparation time can be dramatically reduced.

In the conventional evaluation method, the amount of organic material necessary for the sample preparation is no less than 50 mg. By contrast, in the evaluation method according to the present embodiment, a sample can be prepared from an extremely small amount of organic material, 3-4 mg. The evaluation method according to the present embodiment can be applied for the optimization of the conditions of subsequent processes (such as the heat treatment, solvent, mixed solvent or coating), where a number of parameters can quickly be measured, using only a small amount of sample of the organic material. Whether or not trapping sites exist at the interface with the electrode can also be explored by comparing the performances of the sample with those of an actual device.

As described thus far, the evaluation method according to the present embodiment is effective for quickly diagnosing organic materials for organic solar cells, such as organic thin-film solar cells or dye-sensitized solar cells.

Example

An experiment has been conducted to prove that the photoelectric conversion characteristics of a sample with no electrode formed on it can be directly evaluated by the evaluation system 1 according to Embodiment 1. A stereoregular polythiophene (poly(3-n-hexylthiophene): P3HT) and a fullerene derivative ([6,6]-phenyl-C61-butyric acid methyl ester; PCBM) were used in the experiment, both of which are representative organic materials.

Initially, an organic thin-film solar cell device (Glass/ITO/PEDOT:PSS/BHJ/Ca/Al) with an electrode formed on a BHJ (Bulk Heterojunction) layer of P3HT:PCBM=1:1 was created, and its photoelectric conversion characteristics were evaluated by a conventional evaluation method. Specifically, a method called the "J-V characteristics evaluation of an organic thin-film solar cell under a pseudo-sunlight radiation from a solar simulator" was used as the conventional evaluation method.

Another sample (Quartz/PEDOT:PSS/BHJ) having the aforementioned BHJ layer formed on a quartz substrate with no electrode formed on it was also created (this sample is hereinafter called the "electrode-less sample"). This sample was set in the microwave passing section 7 of the evaluation system 1 shown in FIG. 1. While a 9-GHz microwave was being exposed on the sample, a pulsed laser light having a wavelength of 355 nm was also exposed on the sample, and the photoelectric conversion characteristics of the sample were evaluated. The electrode-less sample was created by spin-coating from a mixed solution of o-dichlorobenzene, chlorobenzene and chloroform within a nitrogen glove box while changing the annealing temperature and time.

Then, the correlation between the evaluation result of the organic thin-film solar cell with the electrode formed on it and that of the electrode-less sample obtained by using the evaluation system 1 was investigated.

Figure 4A:
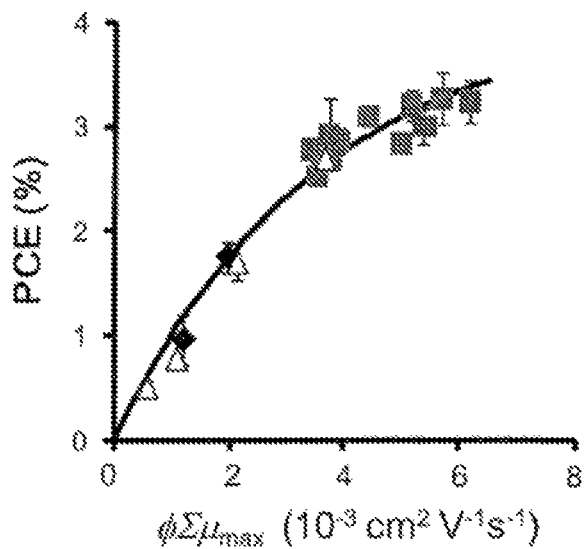
FIG. 4A is a graph showing a relationship between the conversion efficiency of an organic thin-film solar cell device with an electrode formed on it and the peak value of $\phi\Sigma\mu$ obtained when an organic material used in the organic thin-film solar cell device was analyzed by a time-resolved microwave conductivity (TRMC) measurement method.
Figure 4B:
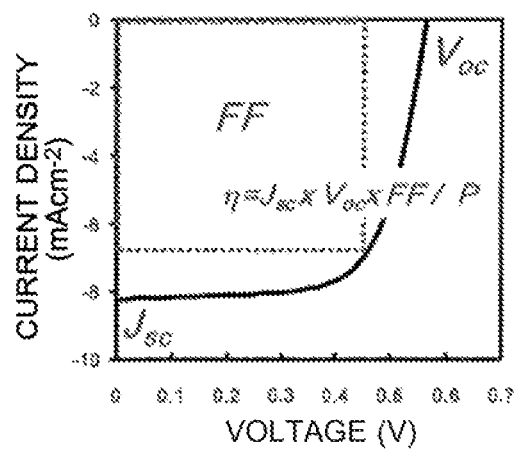
FIG. 4B is a graph showing a measurement result of the electromotive force of the organic thin-film solar cell device.
Figure 4C:
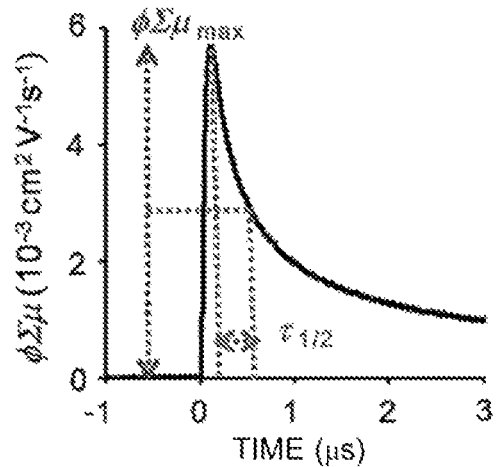
FIG. 4C is a graph showing a measurement result of a TRMC mobility.

FIG. 4A is a graph in which the power conversion efficiency (PCE) of the organic thin-film solar cell device with the electrode formed on it is plotted on the vertical axis and the peak value ($\phi\Sigma\mu_{max}$) of $\phi\Sigma\mu$ is plotted on the horizontal axis, where $\phi\Sigma\mu$ is obtained when the organic material used in the organic thin-film solar cell device is measured by the time-resolved microwave conductivity (TRMC) method. Specifically, "$\phi\Sigma\mu$" is a value obtained by converting, into a physical quantity ($cm^2$/Vs), the difference between the microwave intensity measured when the pulsed laser light is exposed and the same intensity measured when the pulsed laser light is not exposed, where $\phi$ is the charge-carrier generation efficiency due to the exposure of light and $\Sigma\mu$ is the sum of charge-carrier mobilities. FIG. 4B is a graph showing a measurement result of the electromotive force of the organic thin-film solar cell device, with the vertical axis indicating the current density and the horizontal axis indicating the voltage. FIG. 4C is a graph showing a measurement result of a TRMC mobility, with the vertical axis indicating $\phi\Sigma\mu$ obtained by the TRMC method and the horizontal axis indicating the lapse time from the exposure of the pulsed light. FIG. 4A is created on the basis of the results shown in FIGS. 4B and 4C.

PCE is computed by dividing the amount of power generated by the organic thin-film solar cell device by the amount of light energy exposed onto the organic thin-film solar cell device. The parameter $\phi$ is the charge-carrier generation efficiency per one photon absorption at the time resolution of the evaluation system 1, and $\Sigma\mu$ is the sum of the TRMC mobilities of the positive and negative charges. There is a good correlation between PCE and $\phi\Sigma\mu_{max}$. Thus, it has been proven that the evaluation system 1 according to the present embodiment can directly evaluate photoelectric characteristics which reflect the morphology of the BHJ layer.

The effects of impurities and degradation were also evaluated by both the conventional method and the method according to the present embodiment, to investigate the lifetime and intensity of the transient conductivity. The results demonstrated that the evaluation method according to the present embodiment minimizes the effects of impurities and degradation, and enables a quick and easy evaluation of the photoelectric conversion characteristics of an electrode-less sample, thus being effective for the screening of processes and materials.

Second Embodiment

The second embodiment of the present invention is hereinafter described on the basis of FIG. 5.

In the case of evaluating a plurality of samples which have been prepared from the same combination of organic materials with the same mixture ratio of donor and acceptor molecules but have been processed under different conditions (e.g. the annealing temperature and time), a satisfactory evaluation can be made based on a single measurement using a pulsed laser light with a single wavelength. By contrast, in the case of evaluating the samples prepared from the same combination of organic materials with different mixture ratios of the donor and acceptor molecules, or in the case of evaluating the samples made of different combinations of organic materials, the photoelectric conversion characteristics for sunlight or pseudo-sunlight must be measured.

In this respect, the evaluation method according to the first embodiment is disadvantageous since only a single wavelength of the pulsed laser light can be used in one measurement, in order to evaluate an aforementioned kind of sample which requires measuring the photoelectric conversion characteristics for sunlight or pseudo-sunlight (e.g. a sample composed of low band gap polymers with absorption characteristics ranging from shorter to longer wavelengths), it is necessary to change the wavelength of the pulsed laser light and measure the characteristics for each of the different wavelengths of the pulsed laser light. To improve the measurement accuracy, the measurement must be performed a significant number of times while changing the wavelength in small steps. Since the operation of changing the wavelength of the pulsed laser light takes several minutes, the measurement will consume a considerable amount of time and labor.

To address this problem, a xenon flash lamp is adopted in the present embodiment as the pulsed white light source to be used for sample measurement. The xenon flash lamp emits a pulsed white light having a wavelength range close to the sunlight.

Figure 5:
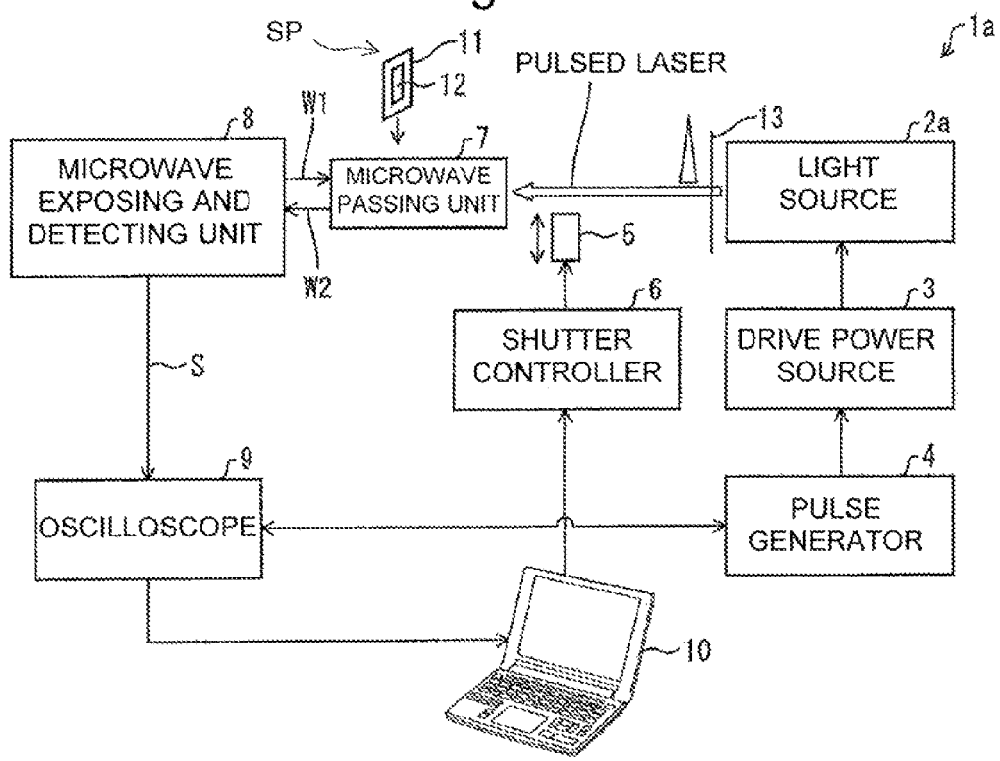
FIG. 5 is a diagram showing the configuration of an evaluation system according to the second embodiment of the present invention.

FIG. 5 is a diagram showing the configuration of the evaluation system 1a according to the present embodiment. The present system differs from the evaluation system 1 shown in FIG. 1 in that the light source 2 is replaced with a light source 2a, with a filter 13 provided between this unit 2a and the microwave passing unit 7. The light source 2a in the present embodiment includes a xenon flashlamp. For convenience of explanation, the components having the same functions as the components already described in the first embodiment are denoted by the same numerals, and their explanation will be omitted.

The evaluation procedure by the evaluation system 1a is same as in the case of the evaluation system 1 shown in FIG. 1. That is to say, with the sample set in the microwave passing unit 7 and the microwave W1 being exposed onto the sample, the light source 2a is driven through the drive power source. As a result, a pulsed white light is exposed from the light source 2a through the filter 13 onto the sample in the microwave passing unit 7. The pulse width of the pulsed laser light is controlled by the pulse generator 4 and can be set, for example, within a range from 10 μs to 1 ms. The time resolution of the pulsed white light can be varied from 10 μs to 1 ms, the white light energy being variable from 0.1 to 100 $mJ/cm^2$/pulse, and the repetition frequency from 0.1 to 20 Hz. The filter 13 is designed to make the spectrum of the pulsed white light emitted from the light source 2a closer to the solar spectrum.

An experiment for determining the optimal mixture ratio of the donor and acceptor molecules in the organic material was conducted with the evaluation system 1a of the present embodiment and the evaluation system 1 of the previously described Embodiment 1. In this experiment, PCPDTBT (poly[2,6-(4,4-bis-(2-ethylhexyl)-4H-cyclopenta[2,1-b; 3,4-b']dithiophene)-alt-4,7-(2,1,3-benzothiadiazole)]) was used as the organic material for the donor molecule, and the fullerene derivative PCBM was used as the organic material for the acceptor molecule.

Figure 6A:
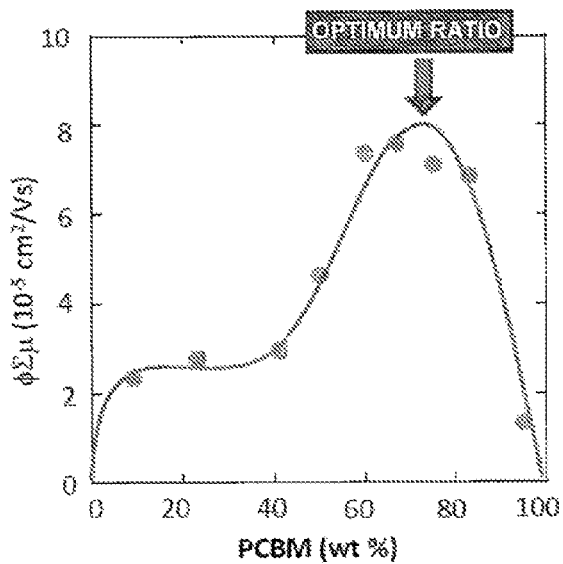
FIG. 6A is a graph showing a relationship between the TRMC signal measured by the evaluation system according to the second embodiment and the mixture ratio of PCBM.
Figure 6B:
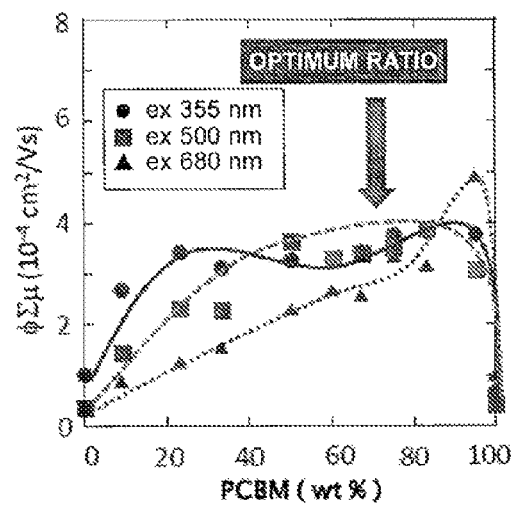
FIG. 6B is a graph showing a relationship between the TRMC signal measured by the evaluation system according to the first embodiment and the mixture ratio of PCBM.
Figure 7:
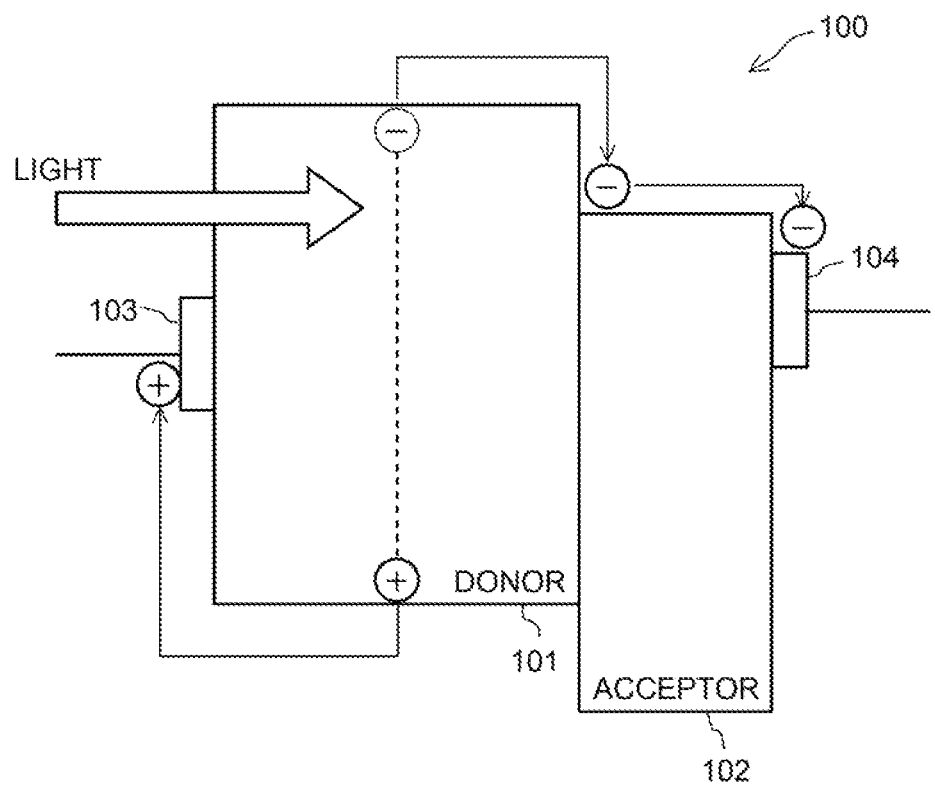
FIG. 7 is a schematic diagram for explaining the principle of photoelectric conversion by a BHJ type organic thin-film solar cell.

FIG. 6A shows the result obtained by using the evaluation system 1a, and FIG. 6B shows the result obtained by using the evaluation system 1. In both FIGS. 6A and 6B, the horizontal axis indicates the percentage of PCBM (percent by weight) and the vertical axis indicates $\phi\Sigma\mu$ obtained in the TRMC method.

In the experiment using the evaluation system 1a, one kind of pulsed white light close to the sunlight was exposed onto the sample by using the xenon flash lamp. The pulsed white light exposed onto the sample in this experiment had a pulse width of approximately 10 μs, a time resolution of approximately 10 μs, a white light energy of 1 $mJ/cm^2$/pulse and a repetition frequency of equal to or higher than 10 Hz. The result demonstrated that the mixture ratio of the PCBM which gave the maximum TRMC signal (i.e. the optimal mixture ratio) was around 75%.

On the other hand, in the experiment using the evaluation system 1, three kinds of pulsed laser light having wavelengths of 355 nm, 500 nm and 680 nm, respectively, were exposed onto the sample. The pulsed laser light had an energy of 25 $mJ/cm^2$/pulse, a repetition frequency of 10 Hz and a pulse width of 5-8 ns, with the other settings of the measurement system being the same as in the experiment of the first embodiment. The result is shown in FIG. 6B, where the filled circles (•) show TRMC signals obtained when the 355-nm pulsed laser light was exposed, the filled squares (■) show TRMC signals obtained when the 500-nm pulsed laser light was exposed, and the filled triangles (▲) show TRMC signals obtained when the 680-nm pulsed laser light was exposed.

As can be seen in FIG. 6B, the mixture ratio of the PCBM which gives the maximum value of the TRMC signal changes depending on the wavelength. This suggests that, in the case of exposing a pulsed laser light on a sample, it is difficult to find the optimal mixture ratio by merely comparing TRMC signals.

In the second embodiment, as in the first embodiment, the sample can be prepared in a short period of time since what is necessary is to merely apply an organic material to a quartz substrate by spin-coating and there is no need to form an electrode. Furthermore, in the evaluation system 1a, since the light source 2a which generates a pulsed white light whose spectrum matches that of pseudo sunlight is used as the light source, it is possible to evaluate photoelectric conversion characteristics which directly reflect device performances corresponding to the sample by exposing only a single kind of light onto each sample and performing the measurement. Therefore, a plurality of samples made of different organic materials can be quickly compared with each other in terms of their photoelectric conversion characteristics.

Accordingly, the evaluation system 1a does not require performing a tedious measurement for one sample while changing the wavelength of the pulsed laser light as in the first embodiment (evaluation system 1), so that the measurement time for one sample can further dramatically be reduced. By the evaluation method using conventional electronic devices, one measurement requires several hours and its reproducibility tends to be low. By the evaluation method according to the present embodiment, a high reproducible evaluation can be made within several minutes.

Thus, the evaluation method according to the present invention is extremely useful as a quick and accurate diagnosing tool for developing various kinds of materials used in organic solar cells, for screening materials, and for optimizing the thin-film formation process. Furthermore, the attenuation dynamics due to the charge carriers can be directly measured, which cannot be measured by the conventional evaluation method. Such a measurement allows the charge-carrier generation efficiency, the charge mobility on a microscopic level and the charge mobility on a macroscopic scale to be separately and individually investigated.

In the previously described embodiments, either a pulsed laser light or a pulsed white light was exposed onto a sample while a microwave was being exposed. A pulsed white light is more suitable in the case of evaluating the performances of an organic thin-film solar cell.

The present invention is not limited to any of the previously described embodiments but can be changed in various ways within the scope of claims. Any embodiment obtained by appropriately combining the technical means separately disclosed in the different embodiments will also be included within the technical scope of the preset invention.

INDUSTRIAL APPLICABILITY

The present invention is suitable for the performance evaluation of organic materials used in organic solar cells, such as organic thin-film solar cells or dye-sensitized solar cells.

EXPLANATION OF NUMERALS

1: Evaluation System
1a: Evaluation System
2: Light Source
2a: Light Source
3: Drive Power Source
4: Pulse Generator
5: Shutter
6: Shutter Controller
7: Microwave Passing Unit
71: Resonation Unit
72: Microwave Introduction Port
73: Pulsed Light Inlet
74, 75: Sample Insertion Opening
8: Microwave Exposing and Detecting Unit
9: Oscilloscope
10: Evaluation Unit
11: Quartz Substrate
12: Organic Material
100: BHJ Type Organic Thin-Film Solar Cell
101: Donor
102: Acceptor
103: Electrode
104: Electrode

The invention claimed is:

1. An evaluation system for evaluating photoelectric conversion characteristics of an organic material used in an organic solar cell, comprising:
a microwave exposing section for exposing a microwave onto the organic material;
a microwave passing section for making the microwave exposure from the microwave exposing section pass through the organic material a plurality of times;
a light source section including a xenon flashlamp, for exposing a pulsed white light having a pulse width within a range from 10 μs to 1 ms onto the organic material;
a microwave detecting section for detecting an intensity of the microwave which has passed through the organic material; and
an evaluating section for evaluating the photoelectric conversion characteristics of the organic material based on the intensity of the microwave which has passed through the organic material when the pulsed white light is exposed and the intensity of the microwave which has passed through the organic material when the pulsed white light is not exposed,
wherein the evaluating section makes an evaluation such that a slower temporal change in a difference between the intensity of the microwave which has passed through the organic material when the pulsed white light is exposed and the intensity of the microwave which has passed through the organic material when the pulsed white light is not exposed indicates better photoelectric conversion characteristics of the organic material.

2. The evaluation system according to claim 1, wherein the evaluating section makes an evaluation such that a larger difference between the intensity of the microwave which has passed through the organic material when the pulsed white light is exposed and the intensity of the microwave which has passed through the organic material when the pulsed white light is not exposed indicates better photoelectric conversion characteristics of the organic material.

3. An evaluation system for evaluating photoelectric conversion characteristics of an organic material used in an organic solar cell, comprising:
a microwave exposing section for exposing a microwave onto the organic material;
a microwave passing section for making the microwave exposure from the microwave exposing section pass through the organic material a plurality of times;
a light source section including a xenon flashlamp, for casting a pulsed white light having a pulse width within a range from 10 μs to 1 ms onto the organic material;

a microwave detecting section for detecting an intensity of the microwave which has passed through the organic material; and an evaluating section for evaluating the photoelectric conversion characteristics of the organic material based on the intensity of the microwave which has passed through the organic material when the pulsed white light is exposed and the intensity of the microwave which has passed through the organic material when the pulsed white light is not exposed, wherein the evaluating section makes an evaluation such that a larger value of a physical quantity $\phi\Sigma\mu$ (cm$^2$/Vs) and a slower temporal change in this physical value indicate better photoelectric conversion characteristics of the organic material, where $\phi$ is a charge-carrier generation efficiency per one photon absorption and $\Sigma\mu$ is a sum of TRMC mobilities of positive and negative charges.

4. An evaluation method for evaluating photoelectric conversion characteristics of an organic material used in an organic solar cell, comprising:

a microwave exposing step, in which a microwave is exposed onto the organic material;

a microwave passing step, in which the microwave exposure in the microwave exposing step is made to pass through the organic material a plurality of times;

a light exposing step, in which a pulsed white light having a pulse width within a range from 10 μs to 1 ms is exposed onto the organic material by using a light exposing unit including a xenon flashlamp;

a microwave detecting step, in which an intensity of the microwave which has passed through the organic material is detected; and an evaluating step, in which the photoelectric conversion characteristics of the organic material are evaluated based on the intensity of the microwave which has passed through the organic material when the pulsed white light is exposed and the intensity of the microwave which has passed through the organic material when the pulsed white light is not exposed, wherein an evaluation in the evaluating step is made such that a slower temporal change in a difference between the intensity of the microwave which has passed through the organic material when the pulsed white light is exposed and the intensity of the microwave which has passed through the organic material when the pulsed white light is not exposed indicates better photoelectric conversion characteristics of the organic material.

5. The evaluation method according to claim 4, wherein an evaluation in the evaluating step is made such that a larger difference between the intensity of the microwave which has passed through the organic material when the pulsed white light is exposed and the intensity of the microwave which has passed through the organic material when the pulsed white light is not exposed indicates better photoelectric conversion characteristics of the organic material.

6. An evaluation method for evaluating photoelectric conversion characteristics of an organic material used in an organic solar cell, comprising:

a microwave exposing step, in which a microwave is exposed onto the organic material;

a microwave passing step, in which the microwave exposure in the microwave exposing step is made to pass through the organic material a plurality of times;

a light exposing step, in which a pulsed white light having a pulse width within a range from 10 μs to 1 ms is exposed onto the organic material by using a light exposing unit including a xenon flashlamp;

a microwave detecting step, in which an intensity of the microwave which has passed through the organic material is detected; and an evaluating step, in which the photoelectric conversion characteristics of the organic material are evaluated based on the intensity of the microwave which has passed through the organic material when the pulsed white light is exposed and the intensity of the microwave which has passed through the organic material when the pulsed white light is not exposed, wherein an evaluation in the evaluating step is made such that a larger value of a physical quantity $\phi\Sigma\mu$ (cm$^2$/Vs) and a slower temporal change in this physical value indicate better photoelectric conversion characteristics of the organic material, where $\phi$ is a charge-carrier generation efficiency per one photon absorption and $\Sigma\mu$ is a sum of TRMC mobilities of positive and negative charges.

* * * * *